United States Patent
Tsugita

(10) Patent No.: US 8,444,665 B2
(45) Date of Patent: May 21, 2013

(54) FILTER FLUSH SYSTEM AND METHODS OF USE

(75) Inventor: Ross S. Tsugita, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1869 days.

(21) Appl. No.: 10/621,972

(22) Filed: Jul. 17, 2003

(65) Prior Publication Data

US 2004/0006370 A1    Jan. 8, 2004

Related U.S. Application Data

(63) Continuation of application No. 09/676,028, filed on Sep. 29, 2000, now Pat. No. 6,620,148, which is a continuation of application No. 09/369,052, filed on Aug. 4, 1999, now Pat. No. 6,168,579.

(51) Int. Cl.
*A61M 29/00* (2006.01)

(52) U.S. Cl.
USPC .......................................................... 606/200

(58) Field of Classification Search
USPC .................. 606/200, 192; 623/1.12, 1.11
See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,447,227 A | 5/1984 | Kotsanis | |

(Continued)

FOREIGN PATENT DOCUMENTS

| | | |
|---|---|---|
| DE | 28 21 048 | 7/1980 |
| DE | 40 30 998 A1 | 10/1990 |

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner* — Gary Jackson
*Assistant Examiner* — Eric Blatt
(74) *Attorney, Agent, or Firm* — Seager, Tufte & Wickhem LLC

(57) ABSTRACT

A filter flush system for temporary placement of a filter in an artery or vein is disclosed. The system typically includes a guidewire insertable within a guiding catheter, which has an occlusion balloon disposed about its distal end. The guidewire has an expandable filter, which can be collapsed to pass through a lumen and distal port of the guiding catheter. The lumen is adapted to receive a variety of endovascular devices, including angioplasty, atherectomy, and stenting catheters. Fluid medium or blood can be infused through the lumen of the guiding catheter to flush embolic material or mobile plaque generated during the endovascular procedures toward the expanded filter deployed downstream from the region of interest. Methods of using the filter flush system to entrap and remove embolic material from the vessel are also disclosed.

22 Claims, 5 Drawing Sheets

U.S. PATENT DOCUMENTS

| | | |
|---|---|---|
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,665,918 A * | 5/1987 | Garza et al. .................... 606/108 |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,832,028 A * | 5/1989 | Patel ............................ 606/194 |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,898,575 A | 2/1990 | Fischell et al. |
| 4,907,336 A | 3/1990 | Gianturco |
| 4,921,478 A | 5/1990 | Solano et al. |
| 4,921,483 A * | 5/1990 | Wijay et al. ................ 604/103.1 |
| 4,921,484 A | 5/1990 | Hillstead |
| 4,926,858 A | 5/1990 | Giffort, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,044 A | 10/1991 | Mueller et al. |
| 5,054,500 A * | 10/1991 | Littleford et al. ............. 600/585 |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vowerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,779,716 A | 7/1998 | Cano et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Sugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,938,672 A | 8/1999 | Nash |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |

| | | | |
|---|---|---|---|
| 6,007,557 A | 12/1999 | Ambrisco et al. | |
| 6,010,522 A | 1/2000 | Barbut et al. | |
| 6,013,085 A | 1/2000 | Howard | |
| 6,022,336 A | 2/2000 | Zadno-Azizi et al. | |
| 6,027,520 A | 2/2000 | Tsugita et al. | |
| 6,051,014 A | 4/2000 | Jang | |
| 6,053,932 A | 4/2000 | Daniel et al. | |
| 6,059,814 A | 5/2000 | Ladd | |
| 6,066,158 A | 5/2000 | Engelson et al. | |
| 6,068,645 A | 5/2000 | Tu | |
| 6,077,295 A | 6/2000 | Limon et al. | |
| 6,080,170 A | 6/2000 | Nash et al. | |
| 6,086,605 A | 7/2000 | Barbut et al. | |
| 6,129,739 A | 10/2000 | Khosravi | |
| 6,135,991 A | 10/2000 | Muni et al. | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,214,026 B1 | 4/2001 | Lepak et al. | |
| 6,231,588 B1 | 5/2001 | Zadno-Azizi | |
| 6,258,115 B1 * | 7/2001 | Dubrul | 606/200 |
| 6,270,477 B1 | 8/2001 | Bagaoisan et al. | |
| 6,295,990 B1 | 10/2001 | Lewis et al. | |
| 6,398,773 B1 | 6/2002 | Bagaoisan et al. | |
| 6,443,926 B1 | 9/2002 | Kletschka | |
| 6,485,500 B1 | 11/2002 | Kokish et al. | |
| 6,540,722 B1 | 4/2003 | Boyle et al. | |
| 6,544,276 B1 | 4/2003 | Azizi | |
| 6,569,148 B2 | 5/2003 | Bagaoisan et al. | |
| 6,605,074 B2 | 8/2003 | Zadno-Azizi et al. | |
| 2001/0049517 A1 | 12/2001 | Zadno-Azizi et al. | |
| 2002/0029031 A1 | 3/2002 | Bagaoisan et al. | |

FOREIGN PATENT DOCUMENTS

| | | |
|---|---|---|
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 * | 5/1999 |
| WO | WO 99/23976 | 5/1999 |
| WO | WO 99/25252 | 5/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Wholey, Mark H. et al., PTA and Stents in the Treatment of Extracranial Circulation, *The Journal of Invasive Cardiology*, 8(E):25E-30E (1996).

* cited by examiner

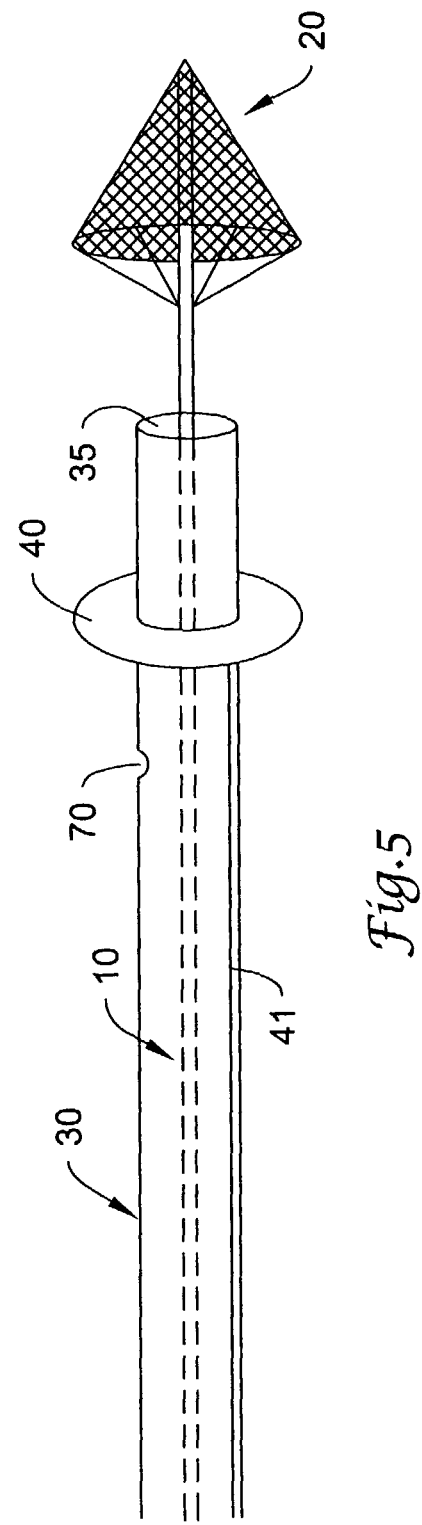

FILTER FLUSH SYSTEM AND METHODS OF USE

This is a continuation of application Ser. No. 09/676,028 filed Sep. 29, 2000 now U.S. Pat. No. 6,620,148, which in turn is a continuation of application Ser. No. 09/369,052 filed Aug. 4, 1999, now U.S. Pat. No. 6,168,579 B1 issued Jan. 2, 2001.

FIELD OF THE INVENTION

The present invention relates generally to devices and methods useful in capturing embolic material in blood vessels. More specifically, the devices and methods provide a vessel filtering system for temporary deployment in arteries such as the carotid arteries and the aorta, and veins such as the subclavian vein and the superior vena cava. The system also includes a guidewire for directing endovascular devices, e.g., atherectomy, stent-deployment, or angioplasty catheters, to a region of interest and a guiding catheter with fluid flushing capability to assist in filtering.

BACKGROUND OF THE INVENTION

Treatment of thrombotic or atherosclerotic lesions in blood vessels using the endovascular approach has recently been proven to be an effective and reliable alternative to surgical intervention in selected patients. For example, directional atherectomy and percutaneous translumenal coronary angioplasty (PTCA) with or without stent deployment are useful in treating patients with coronary occlusion. Atherectomy physically removes plaque by cutting, pulverizing, or shaving in atherosclerotic arteries using a catheter-deliverable endarterectomy device. Angioplasty enlarges the lumenal diameter of a stenotic vessel by exerting mechanical force on the vascular walls. In addition to using the angioplasty, stenting, and/or atherectomy on the coronary vasculature, these endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, occlusion iliac vein thrombosis resistant to thrombolysis.

It is well recognized that one of the complications associated with endovascular techniques is the dislodgment of embolic materials generated during manipulation of the vessel, thereby causing occlusion of the narrower vessels downstream and ischemia or infarct of the organ which the vessel supplies. In 1995, Waksman et al. disclosed that distal embolization is common after directional atherectomy in coronary arteries and saphenous vein grafts. See Waksman et al., American Heart Journal 129(3): 430-5 (1995), incorporated herein by reference. This study found that distal embolization occurs in 28% (31 out of 111) of the patients undergoing atherectomy. In January 1999, Jordan, Jr. et al. disclosed that treatment of carotid stenosis using percutaneous angioplasty with stenting procedure is associated with more than eight times the rate of microemboli seen using carotid endarterectomy. See Jordan, Jr. et al. Cardiovascular surgery 7(1): 33-8 (1999), incorporated herein by reference. Microemboli, as detected by transcranial Doppler monitoring in this study, have been shown to be a potential cause of stroke. The embolic materials include calcium, intimal debris, atheromatous plaque, thrombi, and/or air.

There are a number of devices designed to provide blood filtering for entrapment of vascular emboli. The vast majority of these devices are designed for permanent placement in veins to prevent pulmonary embolism. A temporary venous filter device is disclosed in Bajaj, U.S. Pat. No. 5,053,008 (this and all other references cited herein are expressly incorporated by reference as if fully set forth in their entirety herein). The Bajaj device is an intracardiac catheter for temporary placement in the pulmonary trunk of a patient predisposed to pulmonary embolism due to, e.g. hip surgery, major trauma, major abdominal or pelvic surgery, or immobilization. The Bajaj device includes an umbrella made from meshwork which traps venous emboli before they reach the lungs. This device is designed for venous filtration and is not suitable for arterial use because of the hemodynamic differences between arteries and veins.

There are very few intravascular: devices designed for arterial use. Arteries are much more flexible and elastic than veins and, in the arteries, blood flow is pulsatile with large pressure variations between systolic and diastolic flow. These pressure variations cause the artery walls to expand and contract. Blood flow rates in the arteries vary from about 1 to about 5 L/min. Ginsburg, U.S. Pat. No. 4,873,978, discloses an arterial filtering system, which includes a catheter with a strainer device at its distal end. This device is inserted into the vessel downstream from the treatment site and, after treatment, the strainer is collapsed around the entrapped emboli and removed from the body. The Ginsburg device could not withstand flow rates of 5 L/min. It is designed for only small arteries and therefore could not capture emboli destined for all parts of the body. 1 ng. Walter Hengst GmbH & Co, German Patent DE 34 17 738, also discloses another arterial filter having a folding linkage system which converts the filter from the collapsed to the expanded state.

Filters mounted to the distal end of guidewires have been proposed for intravascular blood filtration. A majority of these devices includes a filter which is attached to a guidewire and is mechanically actuated via struts or a pre-shaped basket which deploy in the vessel. These filters are typically mesh "parachutes" which are attached to the shaft of the wire at the distal end and to wire struts which extend outward in a radial direction on the proximal end. The radial struts open the proximal end of the filter to the wall of the vessel. Blood flowing through the vessel is forced through the mesh thereby capturing embolic material in the filter. A major disadvantage associated with these filter devices is that the filters generally rely on vascular blood flow to push debris into the filters. If blood flow in the vessel becomes restricted, the loosely attached embolic material may not be subjected to normal turbulent blood flow. The embolic particles may stay in the vessel proximal to the filter until the higher normal flow is reestablished (i.e., when the filter is removed), thereby reducing the efficacy of the filtering devices.

Another means of removing embolic material utilizes temporary occlusion devices, such as balloon occlusion catheters and vascular clamps, to isolate a section of a vessel. After blood flow is isolated in the vessel, fluid or blood within the vessel is aspirated to remove embolic debris. One of the disadvantages associated with occlusion devices is that they require temporary cessation or reduction in distal perfusion that may affect oxygenation of distal organs. Shunts may be placed distal to the devices to maintain perfusion to distal organs. However, insertion of the shunts creates additional trauma to the vessel and may generate additional embolic material.

What is needed are simple and safe blood filtering devices which can be temporarily placed in the arteries and veins and can be used with endovascular instruments to effectively prevent distal embolization. Existing devices are inadequate for this purpose.

SUMMARY OF THE INVENTION

Fixed or mobile plaque present in the aorta can dislodge and cause renal infarct or ischemia to other organs. The build up of plaque in the carotid arteries also poses a risk of ischemic stroke by embolization and presents an additional threat of reducing blood flow by occluding the vessel lumen. Plaque present in the iliac and femoral arteries may cause ischemia of the lower extremities, either through distal embolization of atheromatous material or through in situ stenosis of the diseased blood vessel, i.e., narrowing of lumenal diameter. Atherectomy or angioplasty with or without stent deployment in these vessels prevents the above disease from occurring, but can also create these conditions unless the device is specially designed to capture embolic material dislodged during the procedure.

The present invention provides devices and methods for temporary placement of blood filtering capabilities in an artery or vein during endovascular procedures. More specifically, the invention provides a filter flush system which accommodates insertion of endovascular catheters for removing atherosclerotic plaques and/or thrombi and enlarging the lumenal diameter of a stenotic vessel. The filter system also provides means for maintaining distal perfusion during isolation of blood flow, and for pushing embolic debris into the filter during a low-flow state, thereby enhancing filtering capabilities.

In one embodiment, the filter flush system includes an expandable filter, e.g., a parachute, basket, or scroll, mounted on a distal end of a guidewire, and a large diameter catheter (such as a guiding catheter, angiographic catheter, introducer sheath, vessel dilators) having a lumen communicating with a proximal end and a port at its distal end. The distal end of the catheter is adapted for insertion into an artery or vein. The proximal end of the catheter may include a hemostatic valve. An expandable occluder, which may comprise an elastomeric balloon, is disposed about the distal end of the guiding catheter and communicates with an inflation lumen for providing isolation of blood flow in the vessel. The lumen of the catheter is adapted to receive the guidewire, which passes through the distal port. A proximal end of the guidewire will typically be operable from outside the proximal end of the catheter for manipulation of the guidewire independently of the catheter. The lumen of the catheter is also adapted to receive an endovascular device, e.g., an angioplasty, stent-deployment, or atherectomy catheter.

The endovascular catheters typically include a proximal end, a distal end and a lumen which receives the guidewire. An excising member, e.g., a cutting blade, abrasive member, wire cutter, jaws, claws, pincher, snare, etc., is included at the distal region of an atherectomy catheter. An expandable balloon is included at a distal region of an angioplasty catheter. An expandable stent is mounted at a distal region of a stent-deployment catheter. The atherectomy catheter may optionally further include means for intravascular imaging, e.g., an ultrasonic transducer. In certain embodiments, the angioplasty catheters include a stent disposed about the balloon at their distal region. Intravascular imaging devices and stents are fully described in the art and will not be further discussed here.

In another embodiment, the expandable filter comprises an expansion frame and a mesh disposed over the frame. In certain embodiments, the frame comprises a plurality of struts bonded to the guidewire at a first end, and the struts expand radially outward at a second end. The frame may comprise an inflation seal for providing better contact with the vascular walls. The construction and use of expansion means and associated filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, Barbut et al., U.S. application Ser. No. 08/645,762, filed May 14, 1996, and, Barbut et al., U.S. Pat. No. 5,662, 671, and the contents of each of these prior applications are expressly incorporated herein by reference.

In still another embodiment, the guiding catheter includes an infusion port proximal to the occlusion balloon. The port communicates with an infusion lumen in the catheter and is adapted for infusion of fluid or pharmaceutical agents. Using the infusion port, the dosage of pharmaceutical agent required to achieve local effect can be reduced compared to administration by systemic route. Side effects, e.g., hemorrhage associated with systemic administration of t-PA, can also be minimized. In certain embodiments, the angioplasty catheter may include an infusion port proximal to the angioplasty balloon and a perfusion port distal to the balloon. The infusion and perfusion port communicate, respectively, with an infusion and perfusion lumen included in the angioplasty catheter. The infusion port is adapted for aspiration of fluid, blood, air, or vascular debris.

The methods of the present invention include protecting a patient from embolization during an endovascular procedure to remove plaque and/or thrombi from the coronary artery, aorta, common carotid artery, external and internal carotid arteries, brachiocephalic trunk, middle cerebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. The methods also include prevention of distal embolization during an endovascular procedure to remove thrombi and/or foreign bodies in the venous circulation, including the superior vena cava, inferior vena cava, external and internal jugular veins, brachiocephalic vein, pulmonary artery, subclavian vein, brachial vein, axillary vein, iliac vein, renal vein, femoral vein, profinda femoris vein, great saphenous vein, portal vein, splenic vein, hepatic vein, and azygous vein.

In a first method of using the filter flush system, the distal end of the guidewire, having the filter in a collapsed state, is inserted through an artery or vein. The filter and the distal region of the guidewire are positioned in the vessel beyond a region of interest, followed by expansion of the filter. The guiding catheter is inserted over the guidewire, and the occlusion balloon is positioned proximal to the region of interest. The distal region of an atherectomy, stent-deployment, or angioplasty catheter is inserted over the guidewire, where the guidewire is carried within the lumen of the guiding catheter, and advanced to the region of interest. The occlusion balloon is then expanded to isolate blood flow in the vessel while the endovascular catheter removes or otherwise treats the stenotic lesion in the vascular lumen. The catheter may then be withdrawn or left in place, and fluid or blood is infused through the lumen of the guiding catheter to flush embolic debris into the expanded filter. In certain embodiments, the fluid is directed as a jet toward the atheroma for the purpose of blasting the atheroma from the wall of the vessel and thereafter into the filter. The steps of inserting the endovascular catheter and infusing fluid to flush embolic debris may be repeated until an adequate lumenal diameter is established. The filter is then collapsed and removed, together with the captured embolic debris, from the vessel by withdrawing the guidewire. The guiding catheter is withdrawn after the occlusion balloon is deflated.

In another method, after the expanded filter and the guiding catheter are positioned, respectively, in a vessel distal to and proximal from the region of interest, the angioplasty balloon carried by the angioplasty catheter is inflated to dilate the stenotic vascular lumen. Blood, fluid, air, and/or embolic debris present between the occlusion and angioplasty balloon may be aspirated. Alternatively, the occlusion balloon may be deflated during the inflation of the angioplasty balloon to allow blood to be aspirated from the proximal port and passed to the perfusion port distal to the angioplasty balloon, thereby maintaining perfusion to the distal organs during angioplasty.

It will be understood that there are several advantages in using the devices and methods disclosed herein for capturing and removing embolic debris during endovascular procedures. For example, the filter flush system (1) is particularly suited for temporary filtration of blood in any vessel to entrap embolic debris, thereby minimizing neurologic, cognitive, and cardiac complications associated with distal embolization, (2) can withstand high arterial blood flow for an extended time, (3) includes a mesh that is porous enough to allow adequate blood flow in a blood vessel while capturing mobile emboli, (4) is adapted to accommodate an endovascular catheter with or without imaging device, (5) may remove mobile plaque in a vessel by flushing through the guiding catheter, (6) provides means to maintain perfusion to distal organs during endovascular procedures, (7) provide means to administer pharmaceutical agents, e.g., tissue plasminogen activator or nitroglycerin, locally to the region of interest, thereby minimizing side effects associated with systemic administration, and (8) can be used in adult and pediatric patients.

BRIEF DESCRIPTION OF THE DRAWINGS

FIG. 5 depicts another embodiment of the guiding catheter having an infusion port proximal to the occlusion balloon.

DETAILED DESCRIPTION

Figure 1A:
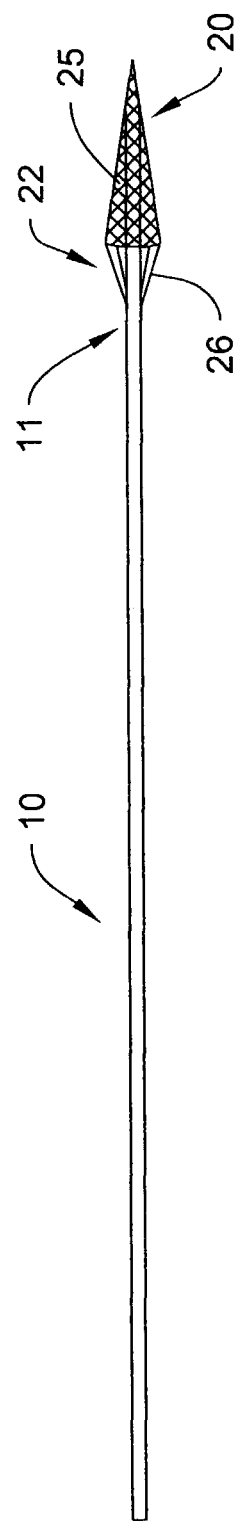
FIG. 1A depicts an embodiment of a collapsed filter mounted on a distal region of a guidewire according to the present invention.
Figure 1B:
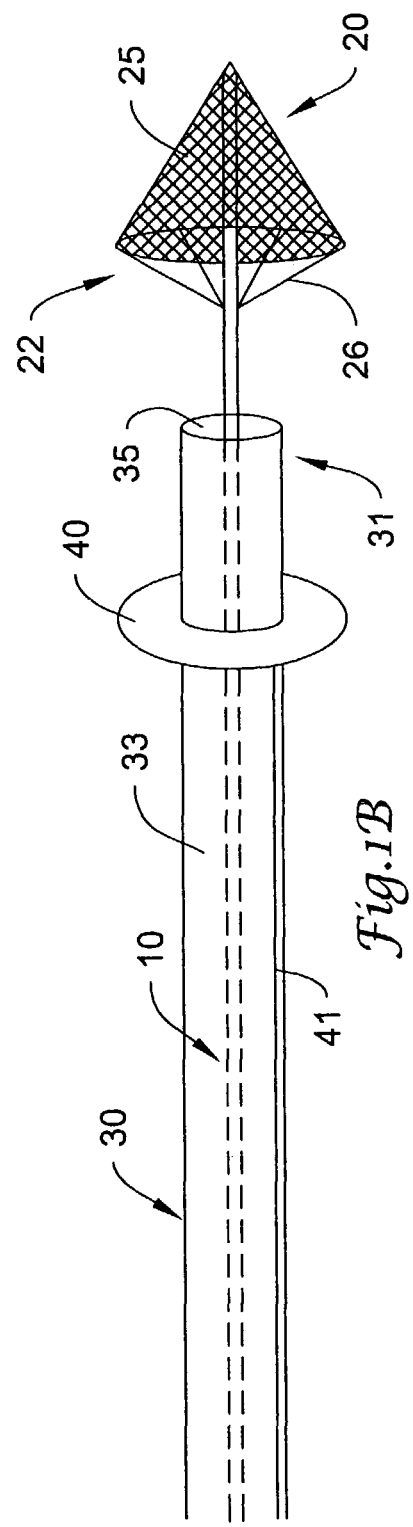
FIG. 1B depicts the guidewire and expanded filter of FIG. 1A inserted through a lumen of a guiding catheter.

In a first embodiment, a filter system for temporary placement in a vessel, either an artery or vein, is provided as depicted in FIGS. 1A and 1B. The filter system includes guidewire 10 having a proximal end, distal end 11, and expandable filter 20 mounted at the distal end. The filter comprises umbrella frame 22 and mesh 25 which is sonic welded or adhesive bonded to arms 26 of the umbrella frame. Anticoagulants, such as heparin and heparinoids, may be applied to mesh 25 to reduce thrombi formation on the mesh. The filter can be collapsed as shown in FIG. 1A to facilitate insertion into a vessel, and thereafter expanded as shown in FIG. 1B. A variety of suitable filter guidewires for use herein are described in Tsugita et al., U.S. Pat. No. 5,910,154, which is incorporated herein by reference in its entirety.

The filter system also includes guiding catheter 30 having lumen 33 communicating with a proximal end and distal end 31, and occlusion balloon 40 disposed about the distal end. Balloon 40 communicates with inflation lumen 41, which is adapted to receive fluid or air for expansion of the balloon. Lumen 33 of the catheter communicates with distal port 35 and is adapted to receive guidewire 10 and other endo'vascular devices, such as atherectomy catheters, endovascular imaging devices, stent-deployment catheters, angioplasty catheters, pressure monitors, electrophysiology catheters, and aspirators.

Figure 2A:
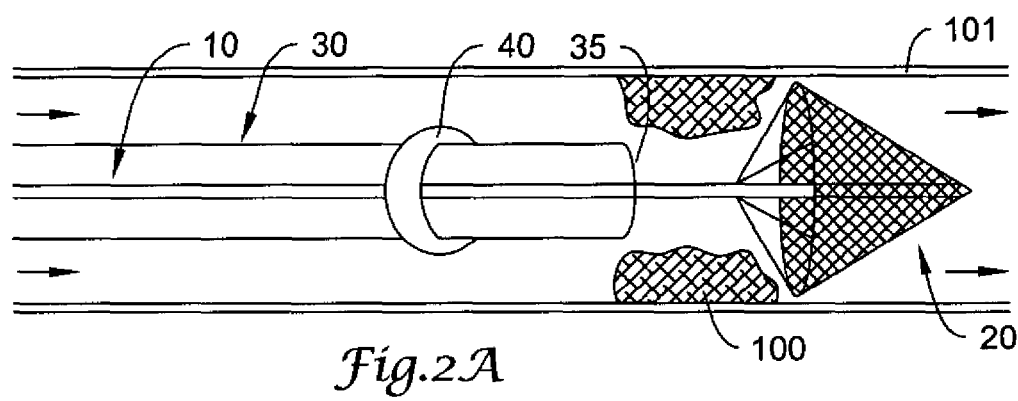
FIG. 2A depicts the filter system of FIG. 1B inserted into a vessel.
Figure 2B:
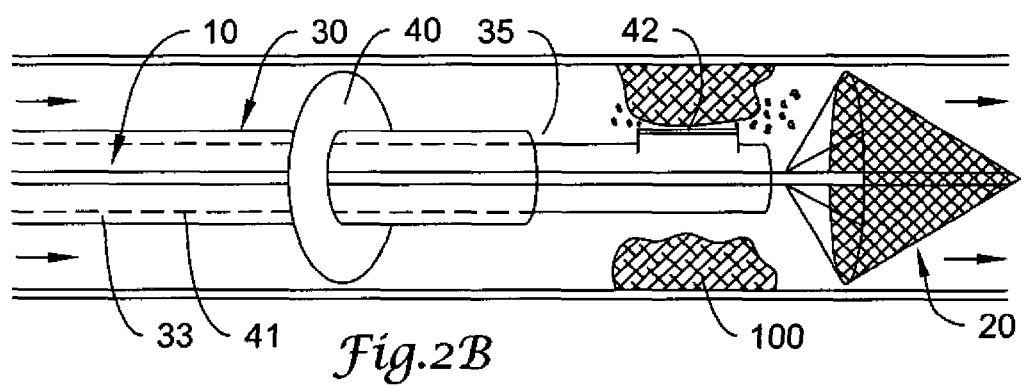
FIG. 2B depicts an atherectomy catheter inserted through the lumen of the guiding catheter of FIG. 2A.
Figure 2C:
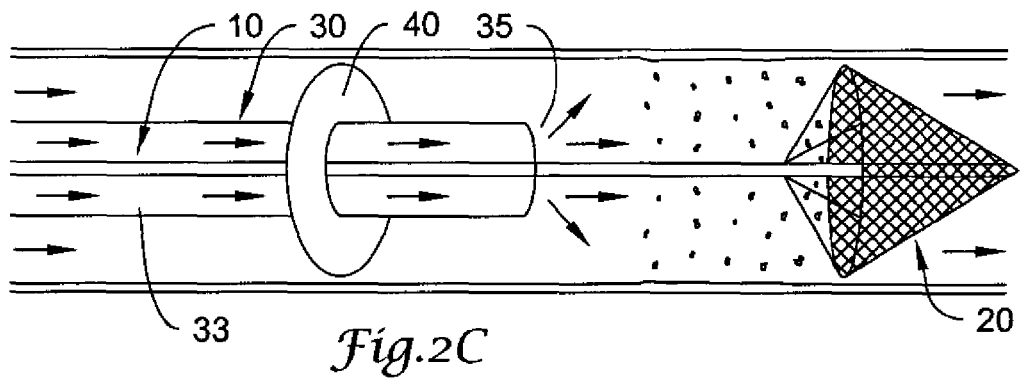
FIG. 2C depicts the filter system of FIG. 2A capturing embolic debris.

In use, as depicted in FIGS. 2A, 2B, and 2C, filter 20 (in the collapsed condition) and distal end 11 of the guidewire is inserted percutaneously through a peripheral artery or vein typically in the direction of blood flow (however, it Is contemplated that guidewire 10 may be inserted in a direction opposite the blood flow). Filter 20 is advanced distal to atheromatous plaque 100 and expanded to contact the vessel walls 101 as depicted in FIG. 2A. Guiding catheter 30 is then inserted over guidewire 10 until distal port 35 is positioned proximal to plaque 100. Atherectomy catheter 41, having atherectomy device 42 mounted on a distal region, is inserted within lumen 33 of the catheter and over guidewire 10. Atherectomy device 42 is advanced distal to port 35 of the catheter to a position adjacent plaque 100. Occlusion balloon 40 is inflated to isolate blood flow in the vessel, while atherectomy device 42 removes plaque 100 as depicted in FIG. 2B.

Figure 2D:
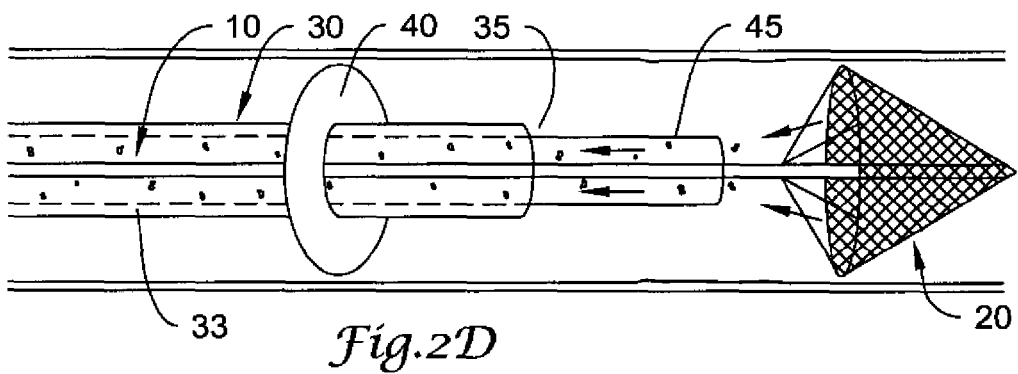
FIG. 2D depicts the filter system of FIG. 2A removing excess embolic debris from the filter.

After adequate lumenal size is achieved by atherectomy, occlusion balloon 40 is deflated, allowing blood flow to be re-established in the region of interest to push the embolic material generated during the procedure toward filter 20 and to perfuse distal organs. Occlusion balloon 40 can be re-inflated to isolate blood flow for repeat atherectomy or other endovascular procedure, e.g., aspiration. After completion of the procedure, the atherectomy catheter is withdrawn from guiding catheter 30 as depicted in FIG. 2C. Fluid or blood is infused through lumen 33 of the guiding catheter to flush the embolic material not cleared as a result of low-flow state toward filter 20. This may be done with or without balloon 40 deployed. The fluid flush may also be directed at the vessel wall to blast free loosely held atheromatous material which remains after atherectomy. In certain cases, the filter may become loaded with excessive amounts of material. In this case, it may be desirable to deploy a separate aspiration catheter 45 through the guiding catheter to extend distally to the filter, and thereby operate to suction embolic material captured in the mesh as depicted in FIG. 2D. Guiding catheter 30 is removed from the vessel. Filter 20 with the captured embolic debris is collapsed and removed from the vessel by withdrawing guidewire 10. The guidewire may alternatively be withdraw into guide catheter 30, and both devices thereafter simultaneously withdrawn. In another embodiment, the guidewire may have a separate capture sheath to assist in its placement and removal by pulling the guidewire into the sheath prior to placement or removal.

By way of example, when the filter system as disclosed herein is intended for use in the aorta, the area of the mesh required for the device is calculated from Bernoulli's equation as described in our earlier applications including Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, and Barbut et al., and U.S. application Ser. No. 08/645,762, filed May 14, 1996, all of which are incorporated herein by reference.

In an embodiment of the filter flush system that is to be used in the aorta, mesh with dimensions within the following ranges is desirable: mesh area is 0.004-5 in$^2$, more preferably 0.007-4 in$^2$, more preferably 0.010-3 in$^2$, more preferably 0.015-2 in$^2$, more preferably 0.020-1 in$^2$, more preferably 0.025-0.076 in$^2$; mesh thickness is 60-280 µm, more preferably 70-270 µm, more preferably 80-260 µm, more preferably 90-250 µm, more preferably 100-250 µm, more preferably 120-230 µm, more preferably 140-200 µm, thread diameter is 30-145 µm, more preferably 40-135 µm, more preferably 50-125 µm, more preferably 60-115 µm, more preferably 70-105 µm and pore size is 500 µm or less, more preferably 400 µm or less, more preferably 300 µm or less, more preferably 200 µm or less, more preferably 100 µm or less, more preferably 50 µm or less and usually larger than at least a red blood cell. In a preferred embodiment of the invention, mesh area is 2-8 in$^2$, mesh thickness is 60-200 µm, thread diameter is 30-100 µm, and pore size is 50-300 µm. In a further preferred embodiment of the invention, mesh area is 3-5 in$^2$, mesh thickness is 60-150 µm, thread diameter is 50-80 µm, and pore size is 100-250 µm.

In other embodiments, the filter comprises a thin film laser cut with holes to allow blood flow. Typical dimensions include pore size of 20-500 µm, a thickness of 0.0005-0.003 inches, and area approximately same as for meshes described above.

Once appropriate physical characteristics are determined, suitable mesh can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is sonic welded into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., monoclonal antibodies such as ReoPro (Centocor). The anticoagulant may be painted or sprayed onto the mesh. A chemical dip comprising the anticoagulant also may be used. Other methods known in the art for applying chemicals to mesh may be used.

Figure 3A:
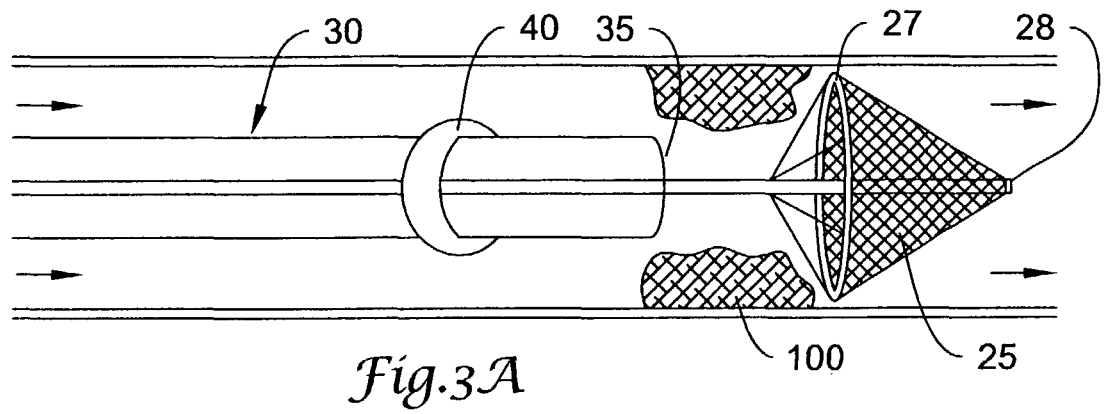
FIG. 3A depicts another embodiment of the filter system including an inflation seal on the filter.
Figure 3B:
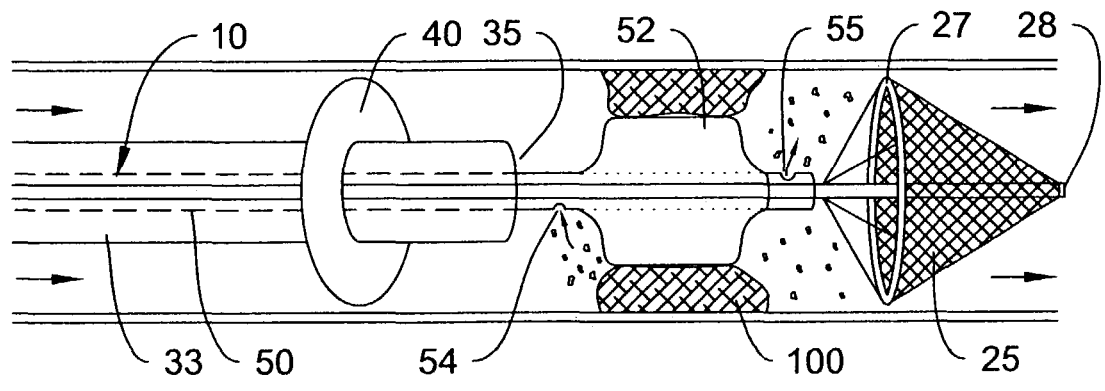
FIG. 3B depicts an angioplasty catheter inserted through the lumen of the guiding catheter of FIG. 3A.
Figure 3C:
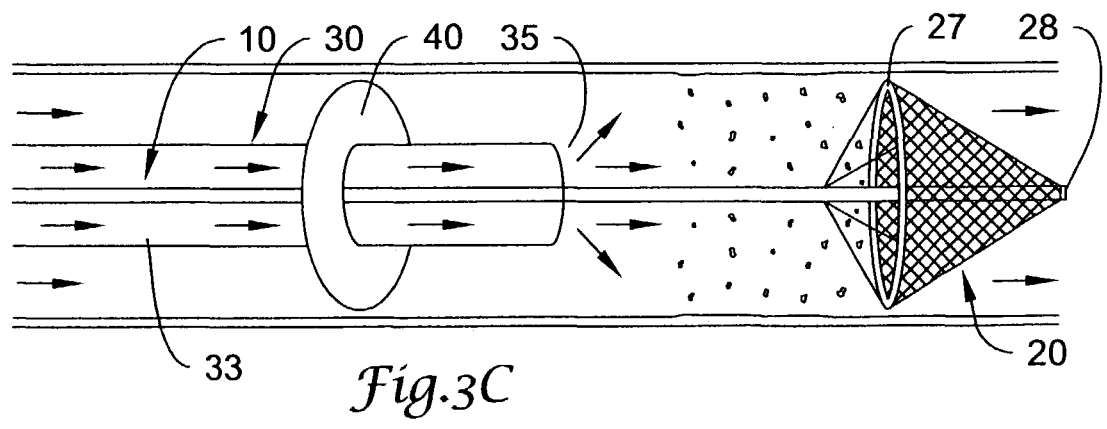
FIG. 3C depicts the filter system of FIG. 3A capturing embolic debris.

FIGS. 3A, 3B, and 3C depict another embodiment of the filter flush system for temporary placement in a vessel. Mesh 25 of filter 20 is operably connected to inflation seal 27 at a first edge and end plate 28 at a second edge. The inflation seal is expandable between a contracted condition and an enlarged condition. In use, in a contracted condition, inflation seal 27 and mesh 25 can be inserted through a peripheral vessel into a region of interest, typically distal to atheromatous plaque 100, as depicted in FIG. 3A. The inflation seal is expanded by injection of fluid or gas to achieve contact with the inner wall of vessel 101. Guiding catheter 30 is inserted over guidewire 10, and distal port 35 is positioned proximal to plaque 100.

Percutaneous translumenal angioplasty has been successful in treating arterial stenosis as well as occlusive venous thrombosis resistant to thrombolysis. See American Heart Journal 125 (2 Pt 1): 362-6 (1993). In FIG. 3B, angioplasty catheter 50, which has angioplasty balloon 52 mounted on a distal region, is inserted through lumen 33 of the guiding catheter over guidewire 10. In a deflated state, the angioplasty balloon is advanced through port 35 to a position adjacent plaque 100. The atheromatous plaque is compressed by inflating balloon 52, thereby dilating the stenosis in the vessel.

In certain embodiments, the angioplasty catheter includes infusion port 54 proximal and perfusion port 55 proximal and distal to balloon 52, respectively. Infusion port 54 may be used to administer pharmaceutical agents, e.g., t-PA or nitroglycerin and to aspirate air, thrombi, plaque, and/or tissue debris. Balloons 40 may be inflated or deflated during angioplasty. Oxygenated medium or blood may be infused through port 55 to provide perfusion to distal organs during angioplasty and facilitate flushing of embolic material into the filter.

In certain embodiments, a prosthesis, such as a stent, is closely associated with the angioplasty balloon. The stent is typically crimped onto the balloon and is capable of controlled radial expansion in a region of interest upon the application of a radial, outwardly extending force from the interior of the stent. The construction of a catheter system carrying a stent is described in detail in Jang et al., U.S. Pat. No. 5,749,848, which is incorporated herein by reference.

The angioplasty catheter may then be withdrawn from the vessel through lumen 33 of the guiding catheter after completion of angioplasty as depicted in FIG. 3C. Occlusion balloon 40 is deflated to re-establish blood flow. Before or after deflation of balloon 40, fluid or blood can be infused through lumen 33 and port 35 to flush embolic material into filter 20. After embolic material is captured and retained in the filter, guiding catheter 30 is removed from the vessel. The filter is then contracted by deflating inflation seal 27 and, with the captured embolic material, is withdrawn from the vessel and removed from the patient's body.

Figure 4A:
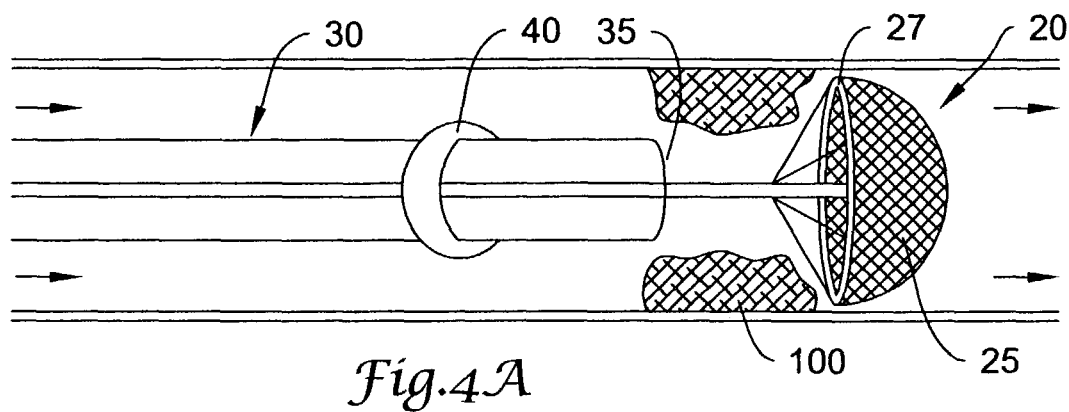
FIG. 4A depicts another embodiment of the filter system having a basket filter.
Figure 4B:
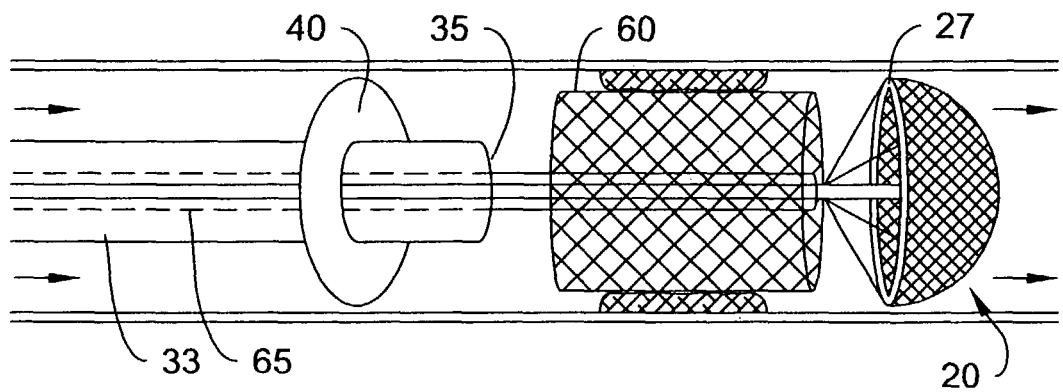
FIG. 4B depicts a stent-deployment catheter inserted through the lumen of the guiding catheter of FIG. 4A.
Figure 4C:
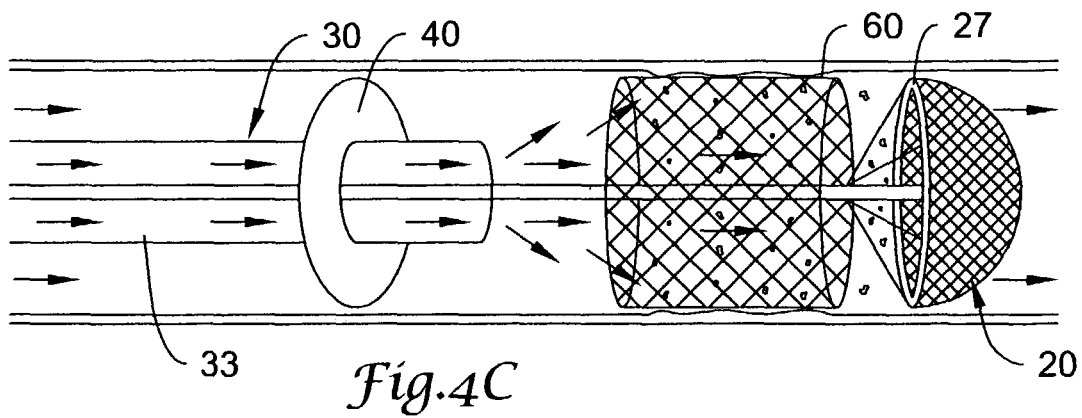
FIG. 4C depicts the filter system of FIG. 4A capturing embolic debris.

Another embodiment of the filter flush system is depicted in FIGS. 4A, 4B, and 4C. Filter 20 is in the form of a pre-shaped basket, having mesh 25 operably connected to inflation seal 27. The inflation seal can be contracted and expanded by infusing gas or fluid. In use, in a contracted condition, inflation seal 27 and mesh 25 are inserted through a peripheral vessel distal to atheromatous plaque 100 as depicted in FIG. 4A. The inflation seal is expanded to contact the inner wall of vessel 101. Guiding catheter 30 is inserted over guidewire 10, having distal port 35 positioned proximal to plaque 100.

Primary stenting for complex atherosclerotic plaque has been efficacious in treating aortic and iliac stenosis that are not amenable to balloon angioplasty. See Onal, et al., Cardiovascular Interventional Radiology 21(5): 386-92 (1998). Catheter intervention to the venous system using expandable metallic stents has been successful in treating superior vena cava syndrome which is mainly associated with malignant tumors and is resistant to any other therapy, including balloon angioplasty and surgery. See Nakanishi, et al., Rinsho Kyoby Geka 14(2): 110-4 (1994). Endovascular catheter 65, which is equipped with self-expanding stent 60 mounted on a distal region, is inserted through lumen 33 of the guiding catheter over guidewire 10 as depicted in FIG. 4B. The stent may be composed of a shape retaining metal, such as nitinol. Catheter 65 will include means for retaining the self-expanding stent. Retaining means may take the form of a sheath disposed about the distal region of the catheter so that the stent is operatively associated with and contained by the sheath, and when the sheath is removed, the stent is released and automatically enlarged to an expanded diameter. Plaque 100 is shown in FIGS. 4B and 4C reduced by the self-expanding and thermally activatable stent 60. The construction and deployment of a self-expanding stent is disclosed in Morgentaler, U.S. Pat. No. 5,224,953, which is expressly incorporated herein by reference.

In FIG. 4C, after stent 60 is deployed over plaque 100, endovascular catheter 65 is removed, leaving lumen 33 of guiding catheter 30 available for infusion of fluid medium. Mobile plaque, which refers to vascular deposits comprising a solidified base and a floppy projection attached to the base which can be dislodged by normal pulsating blood flow, may be found to project through the mesh of stent 60. By flushing fluid through stent 60, the mobile plaque may dislodge and be captured by filter 20. After embolic material is captured and retained in the filter, guiding catheter 30 is removed from the vessel. Filter 20 is contracted, before or after removal of the guiding catheter, by deflating inflation seal 27, and with captured embolic material, is withdrawn from the vessel and removed from the patient's body.

FIG. 5 depicts another embodiment of the filter flush system having infusion port 70, which is located proximal to occlusion balloon 40 and communicates with lumen 33 of guiding catheter 30. Port 70 allows fluid intake and blood to flow from the proximal side of the occlusion balloon and exit distal port 35 of the catheter to provide perfusion to distal organs during an endovascular procedure. In certain embodiments, the guiding catheter may include a plurality of infusion ports proximal to the occlusion balloon, and optionally a one-way valve on the infusion port to eliminate retrograde blood flow. In certain embodiments, the guiding catheter may include aspiration port(s) distal to the occlusion balloon for aspirating vascular debris generated during the endovascular procedure.

The length of the guiding catheter and guidewire will generally be between 15 and 200 centimeters, preferably approximately between 50 and 150 centimeters. The inner diameter of the catheter lumen will generally be between 1.0 and 7 millimeters, preferably approximately between 1.5 and 2.6 millimeters. The diameter of an expanded occlusion balloon will generally be between 1.5 to 50.0 millimeters, preferably approximately between 3.0 and 8.0 millimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, it will be understood that any type of expansion frame disclosed herein or in prior applications can be used with any of the therapeutic catheter interventions, even though any given figure might depict only a particular combination. Moreover, occlusion devices other than balloons can be used with any of the embodiments disclosed herein.

What is claimed is:

1. A medical device for use in a body lumen, the device comprising:
   a first catheter shaft having a proximal end region, a distal end region, and a fluid lumen connecting the proximal end region and the distal end region;
   a second catheter shaft slidably disposed within the first catheter shaft;
   a guidewire slidably disposed in a lumen of the second catheter shaft;
   a filter coupled to the guidewire;
   a balloon coupled to the distal end region of the first catheter shaft;
   a stent disposed adjacent the second catheter shaft,
   wherein the balloon and the first catheter shaft are configured to stop fluid outside of the first catheter shaft proximal to the balloon from flowing distally past the distal region of the shaft when the balloon is expanded;
   wherein the stent is self-expanding and configured to be deployed from a position between the distal end of the first catheter shaft and the filter; and
   wherein the first catheter shaft defines a perfusion lumen configured for the passage of perfusing fluid supplied at the proximal end region therethrough so as to flush embolic debris into the filter.

2. The medical device of claim 1, wherein the second catheter shaft comprises a distal balloon and the stent is disposed about the distal balloon.

3. The medical device of claim 1, wherein the stent is disposed on the second catheter shaft.

4. The medical device of claim 3, wherein the stent is configured to shift between a first generally collapsed configuration and a second generally expanded configuration, and wherein the stent is self-biased to be in the second configuration.

5. The medical device of claim 4, wherein the stent is retained in the first configuration on the second catheter shaft by a retaining sleeve.

6. The medical device of claim 4, wherein the stent is retained in the first configuration on the second catheter shaft by the first catheter shaft.

7. The medical device of claim 4, wherein the self-biased stent is thermally activated.

8. The medical device of claim 1, wherein the device includes a perfusing fluid.

9. The medical device of claim 8, wherein the perfusing fluid is blood.

10. The medical device of claim 8, wherein the perfusing fluid is oxygenated.

11. The medical device of claim 1, wherein the first catheter shaft includes an infusion port within the proximal end region and proximal the balloon.

12. The medical device of claim 11, wherein the infusion port is configured to introduce blood into the perfusion lumen.

13. The medical device of claim 8, wherein the perfusion lumen is configured to direct the perfusing fluid at an inner surface of the body lumen.

14. The medical device of claim 1, wherein the device includes an aspiration catheter configured to remove embolic debris from the filter while the filter is percutaneously disposed in the body lumen.

15. The medical device of claim 14, wherein the aspiration catheter in configured to be slidably disposed in the first catheter shaft.

16. A medical device for use in a body lumen, the device comprising:
   an outer catheter shaft having a proximal end and a distal end;
   an inner catheter shaft slidably disposed in the outer catheter shaft, said inner catheter shaft having a proximal end and a distal end;
   an elongate guidewire slidably disposed in the inner catheter shaft;
   a filter coupled to the guidewire;

a balloon coupled to the outer catheter shaft; and a self-expanding stent coupled to the inner catheter shaft, wherein the balloon and the outer catheter shaft are configured to stop fluid from outside the outer catheter shaft proximal to the balloon from flowing distally past the balloon when the balloon is expanded; and wherein at least one of the inner or outer catheter shafts define a perfusion lumen therein that is configured for perfusing fluid therethrough from an infusion port proximate the proximal end of the shaft so as to flush embolic debris into the filter.

17. The medical device of claim 16, wherein the stent is configured to shift between a first generally collapsed configuration and a second generally expanded configuration, and wherein the stent is biased to be in the second configuration.

18. The medical device of claim 17, wherein the stent is retained in the first configuration on the inner catheter shaft by a retaining sleeve.

19. The medical device of claim 17, wherein the stent is retained in the first configuration on the inner catheter shaft by the outer catheter shaft.

20. The medical device of claim 1, further comprising an aspiration catheter configured for slidable insertion in the first catheter shaft.

21. The medical device of claim 16, further comprising an aspiration catheter configured for slidable insertion in the outer catheter shaft.

22. The medical device of claim 16, further comprising an aspiration catheter configured for slidable insertion in the inner catheter shaft.

\* \* \* \* \*

UNITED STATES PATENT AND TRADEMARK OFFICE
CERTIFICATE OF CORRECTION

PATENT NO. : 8,444,665 B2
APPLICATION NO. : 10/621972
DATED : May 21, 2013
INVENTOR(S) : Ross S. Tsugita Page 1 of 1

It is certified that error appears in the above-identified patent and that said Letters Patent is hereby corrected as shown below:

In the Specifications:

Column 2, Line 28, delete "1 ng." and insert -- Ing. --.

Column 6, Line 63, delete "withdraw" and insert -- withdrawn --.

Column 7, Line 20, delete "140-200 μm" and insert -- 140-210 μm --.

Signed and Sealed this
Sixteenth Day of July, 2013

Teresa Stanek Rea
*Acting Director of the United States Patent and Trademark Office*